United States Patent [19]

Jones et al.

[11] Patent Number: 4,466,981
[45] Date of Patent: Aug. 21, 1984

[54] NAPHTHALENE ANTI-PSORIATIC AGENTS

[75] Inventors: Gordon H. Jones, Cupertino; Michael C. Venuti, San Francisco; John M. Young, Redwood City, all of Calif.

[73] Assignee: Syntex (U.S.A.) Inc., Palo Alto, Calif.

[21] Appl. No.: 437,063

[22] Filed: Oct. 27, 1982

[51] Int. Cl.³ .................. A61K 31/22; A61K 31/275; A61K 31/415; A61K 31/44; A61K 31/505; C07C 69/035; C07C 121/75; C07D 213/55

[52] U.S. Cl. .............................. 424/311; 260/465 D; 424/251; 424/258; 424/263; 424/273 N; 424/273 P; 424/273 R; 424/274; 424/275; 424/285; 424/304; 544/298; 544/318; 544/319; 546/153; 546/294; 546/301; 548/337; 548/346; 548/371; 548/372; 548/375; 548/484; 548/542; 548/543; 548/551; 548/556; 549/23; 549/28; 549/479; 560/139

[58] Field of Search ................ 560/139; 424/311, 304; 260/465 D; 549/28, 23, 500, 479; 548/542, 551, 346, 375, 337, 371, 372, 484, 543, 556; 546/294, 301, 154; 544/318, 319, 298

[56] References Cited

U.S. PATENT DOCUMENTS

| 3,714,206 | 1/1973 | Huemer et al. | 548/337 |
| 4,115,060 | 9/1978 | Finley et al. | 548/337 |
| 4,181,741 | 1/1980 | Bullock | 424/311 |
| 4,229,478 | 10/1980 | Jones et al. | 424/311 |
| 4,255,405 | 3/1981 | Jones et al. | 424/311 |
| 4,321,373 | 3/1982 | Scheler | 548/542 |
| 4,374,855 | 2/1983 | Resnick | 560/139 |

FOREIGN PATENT DOCUMENTS 2258520 8/1973 Fed. Rep. of Germany ...... 560/139

OTHER PUBLICATIONS

*Chemical Abstracts,* vol. 86, Abstract #55193W, Font et al.

*Primary Examiner*—Natalie Trousof
*Assistant Examiner*—Patricia M. Scott
*Attorney, Agent, or Firm*—Annette M. Moore; Tom M. Moran

[57] ABSTRACT

Psoriasis in mammals is relieved by topically administering naphthalenes of the formula:

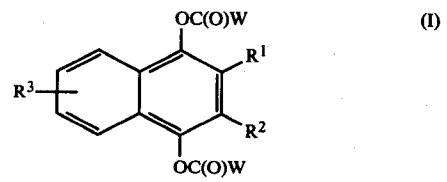

wherein:
$R^1$ and $R^2$ are lower alkoxy or lower alkylthio;
$R^3$ is hydrogen, lower alkyl, lower alkoxy, optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl; optionally substituted phenyl; optionally substituted phenyl lower alkyl; or optionally substituted heterocyclic aryl of three to nine ring atoms containing one or two heteroatoms selected from the group consisting of nitrogen, oxygen and sulfur, and the pharmaceutically acceptable acid addition salts thereof; and n is 0, 1 or 2; and
W is alkyl of one to seven carbon atoms.

22 Claims, No Drawings

NAPHTHALENE ANTI-PSORIATIC AGENTS

BACKGROUND OF THE INVENTION

1. Field of the Invention

The invention relates to naphthalene derivatives which are useful in inhibiting certain dermatological conditions. This invention also relates to pharmaceutical compositions useful in relieving the effects of certain chronic recurrent papulosquamous dermatoses, e.g., psoriasis. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extent, they cause numerous severe undesirable side effects including renal irritation, hepatic toxicity, and erythema.

The compound, 2,3-dimethoxy-1,4-diacetyloxynaphthalene is known and is disclosed to be useful as a synthetic intermediate, but no useful biological activity has been ascribed to it. See J. Chem. Res., Synop. 1980(4), 156-7 and An. Quim. 1976, 72(3):247-53. Certain naphthoquinones are known to be useful in treating psoriasis. See, for example, U.S. Pat. No. 4,229,478 and British Pat. No. 1,243,401. But, these compounds have one or more drawbacks such as causing skin irritation, staining the skin and sensitizing the patient. Surprisingly, it has been discovered that the compounds of the instant invention are less irritating, do not stain the skin and do not sensitize when used in the treatment of psoriasis. Further, the compounds of the present invention are more stable in the topical formulations normally used.

SUMMARY

The present invention relates to a pharmaceutical composition in a form suitable for topical administration to mammals comprising a compound of the following formula

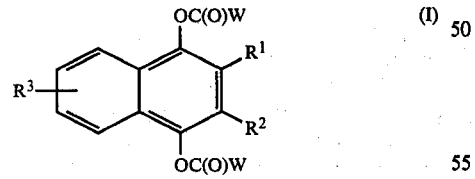

wherein:
$R^1$ and $R^2$ are lower alkoxy of one to six carbon atoms or lower alkylthio of one to six carbon atoms;
$R^3$ is hydrogen, lower alkyl of one to six carbon atoms, lower alkoxy of one to six carbon atoms, optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and
W is alkyl of one to seven carbon atoms.

Another aspect of the invention is a method for relieving the condition of psoriasis in a mammal which comprises topically administering to said mammal a psoriasis-relieving amount of a compound of formula (I).

Another aspect of the invention is the novel compounds of formula (I) wherein $R^1$, $R^2$, $R^3$, W and n are as defined above with the proviso that $R^3$ is not hydrogen when $R^1$ and $R^2$ are methoxy and W is methyl.

Yet another aspect of the invention is preparing compounds of formula (I) by reacting compounds of formula (XI)(infra) with an acid anhydride.

DETAILED DESCRIPTION AND PREFERRED EMBODIMENT

In its broadest aspect, the present invention relates to a pharmaceutical composition in a form suitable for topical administration to mammals comprising a compound of the following formula

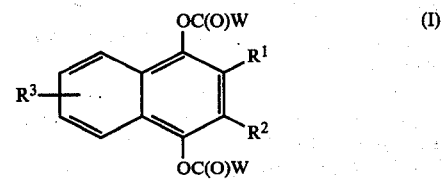

wherein:
$R^1$ and $R^2$ are lower alkoxy of one to six carbon atoms or lower alkylthio of one to six carbon atoms;
$R^3$ is hydrogen, lower alkyl of one to six carbon atoms, lower alkoxy of one to six carbon atoms, optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and
W is alkyl of one to seven carbon atoms.

The present invention also relates to compounds of the formula

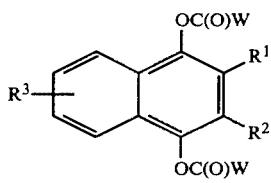

wherein:

R[1] and R[2] are lower alkoxy of one to six carbon atoms or lower alkylthio of one to six carbon atoms;

R[3] is hydrogen, lower alkyl of one to six carbon atoms, lower alkoxy of one to six carbon atoms, optionally substituted phenyl, optionally substituted phenyl lower alkyl, optionally substituted phenyl lower alkoxy, amino, lower alkylamino, lower dialkylamino, halo, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and W is alkyl of one to seven carbon atoms; with the proviso that R[3] is not hydrogen when R[1] and R[2] are methoxy and W is methyl.

More specifically, the present invention relates to compositions containing compounds of formula (I) wherein R[3] is in the 6-position and is hydrogen, bromo, chloro, fluoro or cyano.

An even more specific embodiment of the instant invention are compounds of formula (I) wherein R[3] is at the 6-position and is bromo, chloro, fluoro, cyano, methoxy, ethoxy, n-propoxy, i-propoxy, n-butoxy, and i-butoxy.

Within this specific embodiment of the instant invention, a preferred group of compounds of formula (I) are those wherein R[1] and R[2] are lower alkoxy of one to three carbon atoms and W is lower alkyl of one to five carbon atoms.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, and n-heptyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl lower alkyl" refers to an optionally substituted phenyl ring attached to an alkylene chain of one to six carbon atoms.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl lower alkoxy" refers to a phenyl ring attached to an alkylene chain of one to six carbon atoms having bonded thereto an oxygen atom. Examples of "phenyl lower alkoxy" are benzyloxy, 4-chlorophenylethoxy and phenyl-n-propoxy.

The term "lower alkylthio" refers to a straight or branched chain aliphatic group of one to six carbon atoms having bonded thereto a sulfur moiety. Examples of "lower alkylthio" are methylthio, ethylthio, n-propylthio, i-butylthio an n-hexylthio.

Optionally substituted phenyl refers to a phenyl ring optionally substituted by one or more substituents selected from the group consisting of lower alkyl, lower alkoxy, halo, lower acyl, lower acyloxy, cyano, nitro, amino and lower acylamino.

The term "halo" refers to fluoro, chloro, and bromo. The term "cyano" refers to the group —CN. The term "amino" refers to the group —NH$_2$.

The term "lower alkylamino" refers to an amino group substituted by lower alkyl as is defined above. Examples of "lower alkylamino" are methylamino, ethylamino and n-butylamino.

The term "lower dialkylamino" refers to an amino group substituted by two lower alkyl groups. Examples of "lower dialkylamino" are dimethylamino, dipropylamino and methylethylamino.

The term "lower acyl" refers to the group $R^4C(O)$— wherein R[4] is a lower alkyl group of one to six carbon atoms or an optionally substituted phenyl group. Examples of "lower acyl" are acetyl, propanoyl, butanoyl and benzoyl. The term "lower alkoxycarbonylalkyl" refers to an ester group of the formula $R^5OC(O)$— substituted on an alkyl group wherein R[5] is lower alkyl as is defined above. Examples of "lower alkoxycarbonylalkyl" are methoxycarbonylmethyl, ethoxycarbonylmethyl, ethoxycarbonylethyl, propoxycarbonylethyl and the like.

The term "heterocyclic aryl" is defined as those cyclic aromatic compounds having 3 to 9 ring carbon atoms and having one or two heteroatoms in the ring selected from the group consisting of nitrogen, oxygen and sulfur. Examples of such include the groups thiapyranyl, benzothiapyranyl, furyl, pyrrolyl, imidazolyl, pyrazolyl, pyridinyl, pyrimidinyl, indolyl, quinolinyl, indazolyl and the like. These heterocyclic aryls may be optionally substituted with halo, lower alkyl, cyano and lower alkoxy.

By the term "pharmaceutically acceptable acid addition salts" as used in the case of the various R[3] containing heterocyclic aryl substituents herein is intended to mean those non-toxic pharmaceutically acceptable acid addition salts which do not adversely affect the pharmaceutical properties of the parent compounds. With respect to these addition salts, suitable inorganic anions include, for example, chloride, bromide, iodide, sulfate, phosphate, nitrate, and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

Water/glycol mixture (15% or more glycol): 50–99 parts by weight
Fatty Alcohol: 1–20 parts by weight
Non-ionic Surfactant: 0–10 parts by weight
Mineral Oil: 0–10 parts by weight
Typical Pharmaceutical Adjuvants: 0–5 parts by weight
Active Ingredients: 0.001–10 parts by weight The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolatium, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

White Petrolatum: 40–94 parts by weight
Mineral Oil: 5–20 parts by weight
Glycol Solvent: 1–15 parts by weight
Surfactant: 0–10 parts by weight
Stabilizer: 0–10 parts by weight
Active Ingredients: 0.001–10.0 parts by weight Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

Active Ingredients: 0.001–10.0 parts by weight
Propylene Carbonate: 1–10 parts by weight
Solvent: 1–10 parts by weight
Surfactant: 0–10 parts by weight
White Petrolatum: 70–97 parts by weight Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

Glycol Solvent: 40–35 parts by weight
Fatty Alcohol: 15–45 parts by weight
Compatible Plasticizer: 0–15 parts by weight
Compatible Coupling Agent: 0–15 parts by weight
Penetrant: 0–20 parts by weight
Active Ingredients: 0.001–10.0 parts by weight Another aspect of the invention is a method for relieving the condition of psoriasis in a mammal by topically administering a composition containing a compound of formula (I) wherein $R^3$, n, $R^1$, and $R^2$ are as defined above. Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

PREPARATION

The compounds of formula (I) may be prepared from compounds of formula (V) or (VI).

The intermediates of formula (V) or (VI) wherein $R^3$ is a substituent other than hydrogen may be prepared by the reaction sequence below.

Reaction Sequence I (II) → NO₂-[structure]-Cl,Cl (III) →

(IV) NO₂-[structure with $R^1$, $R^2$] → H₂N-[structure with $R^2$, $R^1$] (V) →

-continued
Reaction Sequence I

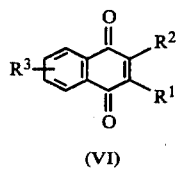

(VI)

wherein $R^1$, $R^2$, and $R^3$ are as defined above.

Compounds of formula (III) are prepared by starting with a 2,3-dihalonaphthoquinone, preferably 2,3-dichloro-1,4-naphthoquinone (compound of formula (II)), which is available from, i.a., Aldrich Chemical Co., and directly nitrating. The reaction proceeds in the manner known for polycyclic aromatic compounds to yield a mixture of the 5- and 6-nitro-2,3-dichloro-1,4-naphthoquinones, compounds of formula (III). The reaction is conducted typically with concentrated nitric acid in a low pH solvent medium, preferably concentrated sulfuric acid, typically at 20° C. to 100° C. for a time sufficient to complete the reaction. Depending on the reaction temperature and times of reaction, ratios of the 5-nitro isomer:6-nitro isomer mixture may range from 10:1 to 1:10, typically 8:1.

Compounds of formula (IV) are synthesized from 5- and 6-nitro-2,3-dichloro-1,4-naphthoquinone, compound of formula (III), by condensing them with an alkali metal alkoxide, wherein the alkoxy moiety is $R^1=R^2$. The reaction is preferably conducted in an inert organic solvent such as tetrahydrofuran, dimethylsulfoxide, dimethylformamide and the like at temperatures from about 20° C. to about 100° C. for a time sufficient to assure completeness of reaction, i.e., for about 2 hours to about 48 hours.

Compounds of formula (IV) wherein $R^1=R^2$ and is lower alkylthio are prepared from compounds of formula (III) in the same manner as for the alkoxy compounds except that an alkali metal salt of an alkyl mercaptan is substituted for an alkali metal alkoxide.

The compounds of formula (V) are prepared from compounds of formula (IV) by catalytic or noncatalytic reduction processes known in the prior art. Metal-acid reducing agent compositions, such as granulated iron and hydrochloric acid, tin and hydrochloric acid, and the like or neutral reducing agent compositions such as zinc dust and aqueous alcohol or aluminum amalgam and aqueous alcohol as well as organo-metallic reducing agents such as lithium aluminum hydride, sodium borohydride and the like may be used in this reduction. Preferably, the reduction is accomplished by treating the compounds of formula (IV) with excess hydrazine in the presence of a catalytically sufficient amount of palladium, typically on carbon. The reaction readily occurs at room temperature, the time of reaction being governed by the rate of addition of the hydrazine to the reaction mixture such typically being about 1 to about 10 hours.

Compounds of formula (VI) wherein $R^3$ is hydrogen may be prepared by reacting compound of formula (II) with an alkali metal alkoxide or alkali metal salt of a mercaptan as described hereinabove.

Compounds of formula (VI) wherein $R^3$ is lower alkylamino or lower dialkylamino are prepared by reacting compounds of formula (V) with an alkyl halide such as methyl iodide by methods well known in the art for alkylating amino groups. The following compounds, for example, may be prepared:

6-methylamino-2,3-dimethoxy-1,4-naphthoquinone;
6-diethylamino-2,3-dimethoxy-1,4-naphthoquinone;
6-ethylmethylamino-2,3-dimethoxy-1,4-naphthoquinone; and
6-methylamino-2,3-dimethylthio-1,4-naphthoquinone.

Compounds of formula (V) are converted into compounds of formula (VI) where $R^3$ is halo by adding to the compound of formula (V) in an acidified aqueous solution, a solution of an alkali metal nitrite. This initial reaction forms the diazonium salt at the 5- or 6-position of the naphthoquinone ring. The salt is decomposed with a solution of cuprous halide dispersed or dissolved in the corresponding halogen acid (the Sandmeyer reaction). This classical reaction is treated extensively in Bigelow, Org. Synthesis, Coll. Vol. I, 126–133 (1941).

A modification of the above Sandmeyer reaction is useful in the preparation of the compounds of formula (VI) where $R^3$ is cyano in that the diazonium salt, rather than being decomposed in the presence of cuprous halide/halogen acid is decomposed in the presence of an alkali metal cyanide and a cuprous halide. See Clarke and Read, Org. Synthesis, Coll. Vol. I, 514 (1941) for a further explanation of the considerations involved in this modified Sandmeyer reaction.

The compounds of formula (VI) where $R^3$ is an optionally substituted heterocyclic arylthio group, optionally substituted phenylthio or alkylthio may also be prepared from the diazonium salt (above). For example, the diazonium salt of the compound of formula (V) is reacted with an alkali solution of thiophenol to yield the compounds of formula (VI) where $R^3$ is phenylthio. Typically, the displacement reaction of the diazonium salt is carried out at 30°–75° C. by adding an alkali solution of thiophenol in an inert organic solvent. Solvents of preference are the inert solvents such as ethyl acetate, tetrahydrofuran and the like. Reaction times may vary from 10 minutes to about 24 hours.

The heterocyclic arylthio compounds are preferably prepared by adding the 2,3-dialkoxy-5 or 6-nitro-1,4-naphthoquinone of formula (IV) to a solution of the thiol-substituted heterocyclic aryl compound admixed with an alkali metal hydride in an inert organic solvent such as dimethylformamide. The reaction is typically conducted at −75° to −25° C. over a period of about 10 to about 60 minutes.

The preferred procedure for the preparation of the compounds of formula (VI) where $R^3$ is a linear or branched alkylthio or an optionally substituted phenylalkylthio is by first converting a compound of formula (V) to the di(2,3-$R^1$,$R^2$-1,4-naphthoquinone)-5 or 6-disulfide of the following formula:

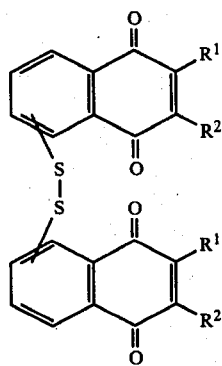

(VII)

wherein $R^1$ and $R^2$ are as defined above. A mixture of an alkaline earth or alkali metal thiol carboxylate such as the acetate, propanoate, butanoate and the like (compounds of the formula

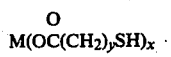

where y is the integer 0 to 18, M is an alkali or alkaline earth metal and x is the valence of said metal) in an inert organic solvent is added to a solution or dispersion of compound of formula (V) at a temperature of $-10°$ to $+10°$ C. over a period of about 1 to about 120 minutes, preferably 5 to 30 minutes. Reaction media include a variety of polar inert solvents such as dimethylformamide, dimethylsulfoxide and the like. After further reaction, typically for about 1 to about 10 hours at 20° to 50° C., the disulfide is isolated. This compound can then be used to prepare the alkyl or phenylalkyl sulfides of formula (VI) by first treating the disulfide with a mixture of sodium borohydride in an inert organic solvent and adding to such mixture at a temperature of about $-10°$ C. to about 75° C. for 1 to 10 hours an appropriate alkylating agent such as a dialkyl sulfate, an alkyl halide, an phenylalkyl halide and the like. Illustrative of such alkylating agents are the compounds methyl bromide, methyl iodide, dimethyl sulfate and benzyl bromide. Preferably alkyl iodide is used as the alkylating agent herein.

Where appropriate, salts of the compounds bearing heterocyclic aryl substituents are prepared. For example, the methylsulfate salt of the 2,3-dialkoxy-5-(pyridin-4-ylthio)-1,4-naphthoquinone is readily prepared by admixture with dimethylsulfate in an inert organic solvent such as tetrahydrofuran. Salt formations of this type are well known in the prior art.

A particularly preferred method of preparing compounds of formula (VI) wherein $R^3$ is 6-halo is shown in the following reaction sequence.

REACTION SEQUENCE II

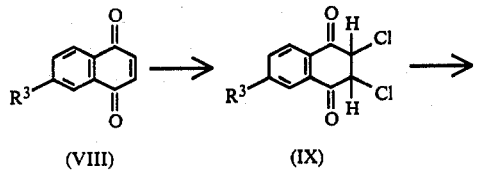

(VIII)      (IX)

-continued
REACTION SEQUENCE II

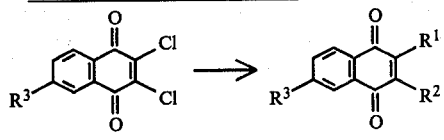

(X)      (VI)

wherein $R^1$ and $R^2$ are as defined above.

Compounds of formula (VIII) are prepared according to the method disclosed in J. Am. Chem. Soc., 70, 3165 (1948) and Ibid., 71, 3615 (1949). Halo substituted butadiene is reacted with 1,4-benzoquinone in a solvent such as acetic acid at a temperature of $-10°$ C. to 30° C., preferably at 25° C. for 24 to 72 hours, preferably from 40 to 48 hours. The 5,7-dihydro compound of formula (VIII) is recovered and treated with an oxidizing agent such as sodium dichromate, sodium nitrite and the like as described in the above articles to form compounds of formula (VIII). Compounds of formula (IX) are prepared by bubbling chlorine gas into a solution of compound of formula (VIII) dissolved in a solvent such as glacial acetic acid, nitrobenzene, carbon tetrachloride and the like, preferably glacial acetic acid at room temperature. This compound, which may be isolated by known means, dissolved in a solvent such as acetic acid is treated with chlorine gas and a suitable catalyst such as sodium acetate, iodine, iron(III)chloride, dimethylformamide or alcohols with heating under reflux for ½ to 4 hours, preferably for 1 to 2½ hours to yield compounds of formula (X). Compounds of formula (VI) wherein $R^3$ is halo are prepared by reacting compound of formula (X) with an alkali metal alkoxide such as sodium alkoxide, e.g., sodium methoxide in an anhydrous solvent such as methanol, dimethylformamide and the like, the solvent being chosen according to the length of the alkyl chain on the alkoxy group. The reaction mixture is heated under reflux for ½ to 3 hours, preferably for ½ to 1½ hours. Compounds of formula (VI) are recovered by conventional means such as by crystallization.

The compounds of formula (VI) wherein $R^1$ and $R^2$ are lower alkylthio may be prepared by the method described for the alkoxy compound except that the alkali metal alkoxide is replaced by the alkali metal salt of the alkyl mercaptan with the solvent being dimethylformamide and the like.

The intermediate, 2-chloro-1,3-butadiene (chloroprene) is available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

The intermediates of formula (VI) wherein $R^3$ is lower alkyl, lower alkoxy, optionally substituted phenyl, optionally substituted phenyl lower alkyl or optionally substituted phenyl lower alkoxy may be prepared by methods well known in the art such as by reacting the diazonium salt of compound of formula (V) with an appropriate compound such as an alcohol e.g. methanol, ethanol, benzyl alcohol and the like. These intermediates may also be prepared by the method set out in Reaction Sequence (II) wherein the 2-halo-1,3-butadiene is replaced by the appropriate 1,3-butadiene such as 2-methyl-1,3-butadiene(isoprene), 2-ethyl-1,3-butadiene and the like.

Compounds of formula (I) are prepared from compounds of formula (VI) by first hydrogenating to form compounds of formula (XI)

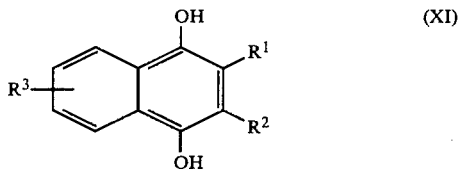

at atmospheric pressure in the presence of a catalyst such as palladium on charcoal and then reacting the hydrogenated compound with an alkanoyl anhydride and pyridine such as acetic anhydride and the like in a solvent such as tetrahydrofuran, diethyl ether and the like. Compounds of formula (I) are recovered by recrystallization.

The sulfinylnaphthalenes of formula (I) are prepared by oxidation of the corresponding thio compounds with a stoichiometric amount of a suitable peracid in an inert organic solvent.

The compounds of formula (I) bearing a sulfonyl substituent are prepared by further oxidizing the compounds of formula (I) wherein $R^3$ is a sulfinyl group with a suitable peracid typically at $-10°$ to $75°$ C. for 1 to 10 hours. Preferably, m-chloroperbenzoic acid in an inert organic solvent at room temperature is used to prepare the desired sulfonyl compounds.

The following specific description is given to enable those skilled in the art to more clearly understand and practice the present invention. It should not be considered as a limitation upon the scope of the invention but merely as illustrative and representative thereof.

Preparation 1

2,3-Dichloro-5- and 6-nitro-1,4-naphthoquinone (Preparation of Compounds of Formula (III))

Finely powdered 2,3-dichloro-1,4-naphthoquinone 50 g. 0.22 mol) was added to a stirred mixture of concentrated sulfuric acid (170 ml) and 90% nitric acid (102 ml) at a rate so that the exothermic reaction raised the temperature to 60° C. The resulting mixture was stirred at 60° C. for a further 2 hours. The yellow crystalline solid was filtered off, washed thoroughly with water and recrystallized from chloroform giving 22.9 g of the 5-nitro isomer, mp 156°–157° C. The above strongly acidic filtrate was poured onto ice water. The resultant solid was filtered off, washed thoroughly with water and dried giving 20.8 g of a mixture of the 5- and 6-isomer. Fractional crystallization of this mixture from acetic acid and chloroform:isopropanol afforded 2.8 g of the 6-nitro isomer, mp 184°–187° C.

Further quantities of both 5- and 6-isomer were obtained from the recrystallization mother liquors by chromatography on a silica gel column eluting with chloroform:cyclohexane mixtures.

Preparation 2

2,3-Dimethoxy-5-nitro-1,4-naphthoquinone (Preparation of Compounds of Formula (IV))

A. A solution of 2,3-dichloro-5-nitro-1,4-naphthoquinone (2.72 g, 10 mmol) in anhydrous tetrahydrofuran (15 ml) was added to a solution of 1N sodium methoxide (25 ml, 25 mmol) and the resulting solution stored at 22° for 16 hours. Acetic acid (1 ml) was then added, the solution concentrated in vacuo and the residue partitioned between water (50 ml) and chloroform (100 ml). The aqueous phase was further extracted with chloroform (2×50 ml). The combined chloroform extracts were dried with MgSO$_4$ and concentrated in vacuo. The residue was recrystallized from methanol giving 1.99 g of 2,3-dimethoxy-5-nitro-1,4-naphthoquinone, mp 156°–157°.

B. Similarly, using the above procedure in Part A, substituting 2,3-dichloro-6-nitro-1,4-naphthoquinone, where appropriate, for 2,3-dichloro-5-nitro-1,4-naphthoquinone and the appropriate sodium alkoxide for sodium methoxide, the following compounds are prepared:

2,3-dimethoxy-6-nitro-1,4-naphthoquinone, mp 113°–114° C.;
2,3-diethoxy-5-nitro-1,4-naphthoquinone;
2,3-diethoxy-6-nitro-1,4-naphthoquinone;
2,3-di-n-propoxy-5-nitro-1,4-naphthoquinone;
2,3-di-n-propoxy-6-nitro-1,4-naphthoquinone;
2,3-di-i-propoxy-5-nitro-1,4-naphthoquinone;
2,3-di-i-propoxy-6-nitro-1,4-naphthoquinone;
2,3-di-n-butoxy-5-nitro-1,4-naphthoquinone;
2,3-di-n-butoxy-6-nitro-1,4-naphthoquinone;
2,3-di-s-butoxy-5-nitro-1,4-naphthoquinone;
2,3-di-s-butoxy-6-nitro-1,4-naphthoquinone;
2,3-di-n-pentyloxy-5-nitro-1,4-naphthoquinone;
2,3-di-n-pentyloxy-6-nitro-1,4-naphthoquinone;
2,3-di-s-pentyloxy-5-nitro-1,4-naphthoquinone;
2,3-di-s-pentyloxy-6-nitro-1,4-naphthoquinone;
2,3-di-n-hexyloxy-5-nitro-1,4-naphthoquinone;
2,3-di-n-hexyloxy-6-nitro-1,4-naphthoquinone;
2,3-di-i-hexyloxy-5-nitro-1,4-naphthoquinone;
2,3-di-i-hexyloxy-6-nitro-1,4-naphthoquinone;
2,3-di(2,2-dimethylpropoxy)-5-nitro-1,4-naphthoquinone; and
2,3-di(2,2-dimethylpropoxy)-6-nitro-1,4-naphthoquinone.

C. Similarly, using the above procedure in Part A, substituting 2,3-dichloro-6-nitro-1,4-naphthoquinone, where appropriate, for 2,3-dichloro-5-nitro-1,4-naphthoquinone and the appropriate sodium salt of alkylmeracaptan for sodium methoxide, the following compounds, for example, are prepared:
2,3-dimethylthio-6-nitro-1,4-naphthoquinone;
2,3-di-i-propylthio-6-nitro-1,4-naphthoquinone; and
2,3-di-n-hexylthio-6-nitro-1,4-naphthoquinone.

Preparation 3

2,3-Dimethoxy-5-amino-1,4-naphthoquinone (Preparation of Compounds of Formula (V))

Hydrazine (4.0 ml, 125 mmol of 97%) was added dropwise, over a 2 hour period, to a stirred mixture of the captioned compound of Preparation 2 (19.9 g, 75.6 mmol), 5% palladium on carbon (10 g) and ethanol (750 ml) in a nitrogen atmosphere. The catalyst was filtered off through a celite pad that was washed with hot ethanol (2×300 ml). The combined filtrate and washings were concentrated to dryness in vacuo and the residue recrystallized from water:ethanol (1.5:1) giving 14.6 g of 2,3-dimethoxy-5-amino-1,4-naphthoquinone, mp 116°–117°.

Similarly, substituting the compounds from Preparation 2 for 2,3-dimethoxy-5-nitro-1,4-naphthoquinone the following compounds are prepared:
2,3-dimethoxy-6-amino-1,4-naphthoquinone, mp 196°–197° C.;
2,3-diethoxy-5-amino-1,4-naphthoquinone;
2,3-diethoxy-6-amino-1,4-naphthoquinone;
2,3-di-n-propoxy-5-amino-1,4-naphthoquinone;
2,3-di-n-propoxy-6-amino-1,4-naphthoquinone;
2,3-di-i-propoxy-5-amino-1,4-naphthoquinone;
2,3-di-i-propoxy-6-amino-1,4-naphthoquinone;
2,3-di-n-butoxy-5-amino-1,4-naphthoquinone;
2,3-di-n-butoxy-6-amino-1,4-naphthoquinone;
2,3-di-s-butoxy-5-amino-1,4-naphthoquinone;
2,3-di-s-butoxy-6-amino-1,4-naphthoquinone;
2,3-di-n-pentyloxy-5-amino-1,4-naphthoquinone;
2,3-di-n-pentyloxy-6-amino-1,4-naphthoquinone;
2,3-di-s-pentyloxy-5-amino-1,4-naphthoquinone;
2,3-di-s-pentyloxy-6-amino-1,4-naphthoquinone;
2,3-di-n-hexyloxy-5-amino-1,4-naphthoquinone;
2,3-di-n-hexyloxy-6-amino-1,4-naphthoquinone;
2,3-di-i-hexyloxy-5-amino-1,4-naphthoquinone;
2,3-di-i-hexyloxy-6-amino-1,4-naphthoquinone;
2,3-di(2,2-dimethylpropoxy)-5-amino-1,4-naphthoquinone;
2,3-di(2,2-dimethylpropoxy)-6-amino-1,4-naphthoquinone;
2,3-dimethylthio-6-amino-1,4-naphthoquinone;
2,3-di-i-propylthio-6-amino-1,4-naphthoquinone; and
2,3-di-n-hexylthio-6-amino-1,4-naphthoquinone.

Preparation 4

5-Chloro-2,3-dimethoxy-1,4-naphthoquinone (Preparation of Compounds of Formula (VI) where $R^3$ is 5-chloro)

A solution of sodium nitrate (0.69 g, 10 mmol) in water (5 ml) was added at 0°–5° C. to a solution of 5-amino-2,3-dimethoxy-1,4-naphthoquinone (1.17 g, 5 mmol) in 5:1 acetic acid:water (25 ml) containing concentrated hydrochloric acid (1.7 ml). A further quantity of sodium nitrite (0.69 g) was then added to the reaction mixture after cooling to −5° C., followed by a solution of cuprous chloride (0.6 g) in concentrated hydrochloric acid (5 ml). The mixture was allowed to warm to 22° C. and solid cuprous chloride was added portionwise until the mixture assumed a green color. Water was then added to the reaction mixture and the precipitated yellow solid filtered off, washed with water and recrystallized from methanol:water (2:1) giving 1.01 g of 5-chloro-2,3-dimethoxy-1,4-naphthoquinone, mp 120°–121° C.

Similarly, proceeding as above substituting the appropriate compounds for 2,3-dimethoxy-5-amino-1,4-naphthoquinone the following compound are prepared:
6-chloro-2,3-dimethoxy-1,4-naphthoquinone;
5-chloro-2,3-diethoxy-1,4-naphthoquinone;
6-chloro-2,3-diethoxy-1,4-naphthoquinone;
5-chloro-2,3-di-n-propoxy-1,4-naphthoquinone;
6-chloro-2,3-di-n-propoxy-1,4-naphthoquinone;
5-chloro-2,3-di-i-propoxy-1,4-naphthoquinone;
6-chloro-2,3-di-i-propoxy-1,4-naphthoquinone;
5-chloro-2,3-di-n-butoxy-1,4-naphthoquinone;
6-chloro-2,3-di-n-butoxy-1,4-naphthoquinone;
5-chloro-2,3-di-s-butoxy-1,4-naphthoquinone;
6-chloro-2,3-di-s-butoxy-1,4-naphthoquinone;
5-chloro-2,3-di-n-pentyloxy-1,4-naphthoquinone;
6-chloro-2,3-di-n-pentyloxy-1,4-napthoquinone;
5-chloro-2,3-di-s-pentyloxy-1,4-naphthoquinone;
6-chloro-2,3-di-s-pentyloxy-1,4-naphthoquinone;
5-chloro-2,3-di-n-hexyloxy-1,4-naphthoquinone;
6-chloro-2,3-di-n-hexyloxy-1,4-naphthoquinone;
5-chloro-2,3-di-i-hexyloxy-1,4-naphthoquinone;
6-chloro-2,3-di-i-hexyloxy-1,4-naphthoquinone;
5-chloro-2,3-di(2,2-dimethylpropoxy)-1,4-naphthoquinone;
6-chloro-2,3-di(2,2-dimethylpropoxy)-1,4-naphthoquinone;
6-methoxy-2,3-dimethoxy-1,4-naphthoquinone;
6-ethoxy-2,3-diethoxy-1,4-naphthoquinone;
6-i-butoxy-2,3-dimethoxy-1,4-naphthoquinone;
6-phenylethoxy-2,3-dimethoxy-1,4-naphthoquinone;
6-chloro-2,3-dimethylthio-1,4-naphthoquinone;
6-chloro-2,3-di-i-propylthio-1,4-naphthyloqinone; and
6-chloro-2,3-di-n-hexylthio-1,4-naphthyloqinone;

Preparation 5

5-Cyano-2,3-dimethoxy-1,4-naphthoquinone (Preparation of Compounds of Formula (VI) where $R^3$ is cyano)

A solution of sodium nitrite (2.21 g, 32 mmol) in water (6 ml) was added at 0°–5° C. to a stirred suspension of 5-amino-2,3-dimethoxy-1,4-naphthoquinone (3.73 g, 16 mmol) in 3:1 water:tetrahydrofuran (20 ml) containing concentrated hydrochloric acid (6.7 ml) and the resulting mixture was stirred at 0°–5° C. for a further 1¼ hour. The almost clear solution is then neutralized with sodium carbonate, filtered and added at 5° C. to a vigorously stirred solution of cuprous chloride (4.75 g) and sodium cyanide (5.88 g) in water (80 ml). Ethyl acetate (100 ml) was added and the mixture is heated at 45° C. for 0.5 hours, filtered through a celite bed and separated into the two phases. The aqueous phase was extracted with ethyl acetate (2×100 ml). The combined organic phases were extracted with brine (150 ml), dried over MgSO$_4$ and concentrated to dryness in vacuo. The residue was recrystallized from isopropanol giving 2.96 g of 5-cyano-2,3-dimethoxy-1,4-naphthoquinone, mp 171°–172° C.

Similarly, proceeding as above the following compound is prepared:
6-cyano-2,3-dimethoxy-1,4-naphthoquinone.

Preparation 6

Di-(2,3-dimethoxy-1,4-naphthoquinone-5)-disulfide (Preparation of Compounds of Formula (VII))

A slurry of potassium thiolacetate (1.5 g, 13.1 mmol) in dimethylformamide (25 ml) was added over 10 minutes to a solution at 0°–5° C. of 5-amino-2,3-dimethoxy-1,4-naphthoquinone (2.63 g, 10 mmol) in dimethylformamide (25 ml). The mixture was allowed to warm to 22° C. and, after 2 hours, an additional quantity of potassium thiolacetate (1.25 g) was added. After a further 45 minute reaction, the mixture was added to ice water (500 ml) that was adjusted to pH 6 with acetic acid. The precipitated solid was filtered off, washed with water and recrystallized from chloroform:methanol (1:1) giving 1.32 g. of di(2,3-dimethoxy-1,4-naphthoquinone-5)-disulfide, mp 220°–221° C.

Preparation 7

2,3-Dimethoxy-5-phenylthio-1,4-naphthoquinone (Preparation of Compounds of Formula (VI) where $R^3$ is phenylthio)

Method A. Sodium nitrite (0.18 g) was added at 0°–5° C. to a stirred suspension of 5-amino-2,3-dimethoxy-1,4-naphthoquinone (233 mg, 1 mmol) in 0.6N hydrochloric acid (10 ml) and tetrahydrofuran (1 ml). The mixture was stirred at 5° C. for 10 minutes until a clear solution was obtained and was then neutralized by the addition of sodium carbonate. The ice cold solution was then slowly added to a vigorously stirred two-phase mixture in a nitrogen atmosphere at 50° C. composed of potassium hydroxide (0.16 g), water (10 ml), thiophenol (0.32 ml) and ethyl acetate (35 ml). After a total reaction time of 20 min, the mixture was partitioned between ethyl acetate (40 ml) and brine (100 ml). The ethyl acetate phase was dried over $MgSO_4$ and concentrated in vacuo. The residue was purified by chromatography on a thick layer silica gel plate using acetone:toluene:chloroform (1:20:20) giving a solid that, after recrystallizing from isopropanol, afforded 70 mg of 2,3-dimethoxy-5-phenylthio-1,4-naphthoquinone, mp 76°–77° C.

Similarly, using imidazolyl-2-thiol in place of thiophenol, 2,3-dimethoxy-5-(imidazol-2-yl)thio-1,4-naphthoquinone, mp 97°–100° C., was prepared.

Method B. Thiophenol (6.0 ml, 59 mmol) was added at −30° C. to a stirred mixture of 100% sodium hydride (1.4 g, 59 mmol) and dimethylformamide (200 ml) and the resulting mixture was stirred at 22° C. for 16 hours. This mixture was then cooled to −50° C. and a solution of di(2,3-dimethoxy-1,4-naphthoquinone-5)-disulfide (13.0 g, 49 mmol) in dimethylformamide (100 ml) was added over 30 min. The resulting mixture was allowed to warm to 22° C. over 1 hour before being cooled to −50° C. and neutralized with acetic acid (5.4 ml, 90 mmol). The reaction mixture was then poured into a mixture of water (1.8 l) and methanol (700 ml). The precipitated material was filtered off and recrystallized from methanol giving 10.3 g of 2,3-dimethoxy-5-phenylthio-1,4-naphthoquinone, mp 76°–79° C. A further amount (2.2 g) mp 76°–77° C. was obtained in a second crop from the recrystallization.

Similarly, substituting of the appropriate thiol for thiophenol and the appropriate compound from Preparation 3, the following compounds are prepared:

2,3-dimethoxy-6-(2-chlorophenylthio)-1,4-naphthoquinone;
2,3-dimethoxy-5-(3-chlorophenylthio)-1,4-naphthoquinone, mp 125°–126° C.;
2,3-dimethoxy-6-(4-chlorophenylthio)-1,4-naphthoquinone;
2,3-dimethoxy-5-(2,6-dichlorophenylthio)-1,4-naphthoquinone, mp 158°–159° C.;
2,3-dimethoxy-5-(4-fluorophenylthio)-1,4-naphthoquinone, mp 124°–125° C.;
2,3-dimethoxy-5-(2-bromophenylthio)-1,4-naphthoquinone, mp 152°–153° C.;
2,3-dimethoxy-6-(4-bromophenylthio)-1,4-naphthoquinone;
2,3-diethoxy-6-(4-methoxyphenylthio)-1,4-naphthoquinone;
2,3-di-n-propoxy-6-(4-nitrophenylthio)-1,4-naphthoquinone;
2,3-di-n-butoxy-6-(2-ethylphenylthio)-1,4-naphthoquinone;
2,3-di-n-pentyloxy-6-pyridin-2-ylthio-1,4-naphthoquinone;
2,3-di-n-hexyloxy-6-pyridin-4-ylthio-1,4-naphthoquinone; and
2,3-dimethoxy-5-(4-acetylaminophenylthio)-1,4-naphthoquinone, mp 118°–127° C.

Preparation 8

2,3-Dimethoxy-5-methylthio-1,4-naphthoquinone (Preparation of Compounds of Formula (VI) where $R^3$ is methylthio)

Sodium borohydride (100 mg) was added portionwise to a stirred suspension of di(2,3-dimethoxy-1,4-naphthoquinone-5)-disulfide (0.5 g, 1 mmol) in 7:1 tetrahydrofuran:isopropanol (40 ml) in a nitrogen atmosphere until TLC analysis indicated that no starting material remains. Methyl iodide (0.2 ml) was then added and, after 5 minutes, the reaction mixture was poured into ice water (300 ml). 10% Ferric chloride (10 ml) was subsequently added. The precipitated solid was filtered off, washed with water and recrystallized from isopropanol giving 0.36 g of 2,3-dimethoxy-5-methylthio-1,4-naphthoquinone, mp 112°–113° C.

By substituting other alkyl iodides for methyl iodide the following are prepared;

2,3-dimethoxy-6-methylthio-1,4-naphthoquinone;
2,3-dimethoxy-5-benzylthio-1,4-naphthoquinone, m.p. 142°–143° C.;
2,3-dimethoxy-6-ethylthio-1,4-naphthoquinone; and
2,3-dimethoxy-5-methoxycarbonylmethylthio-1,4-naphthoquinone, m.p. 119°–120° C.

Preparation 9

2,3-Dimethoxy-5-(4-methylpyridiniumthio)-1,4-naphthoquinone methyl sulfate

A mixture of dimethylsulfate (0.19 ml, 2 mmol) and 2,3-dimethoxy-5-(4-methylpyridinylthio)-1,4-naphthoquinone (327 mg, 1 mmol) in tetrahydrofuran (10 ml) was heated under reflux for 3 hours and then cooled to 20° C. The orange solid was filtered off, washed with tetrahydrofuran and recrystallized from ethanol:isopropanol giving 279 mg of 2,3-dimethoxy-5-(4-methylpyridiniumthio)-1,4-naphthoquinone methyl sulfate mp 160°–162° C. and a second crop of 110 mg.

Similarly prepared is 2,3-dimethoxy-5-(2-methylpyridiniumthio)-1,4-naphthoquinone methyl sulfate.

Similarly, the following compounds are prepared by the above method:

2,3-dimethoxy-5-(2-methylpyridiniumsulfinyl)-1,4-naphthoquinone methyl sulfate, m.p. 175°–176° C.; and
2,3-diemthoxy-5-(4-methylpyridiniumsulfinyl)-1,4-naphthoquinone methyl sulfate, m.p. 175°–176° C.

Preparation 10

(Preparation of compounds of formula (X) wherein $R^3$ is 6-chloro)

Into a solution of 6-chloro-1,4-naphthoquinone (193 g) in glacial acetic acid (1600 mL) was bubbled chlorine gas until TLC of an aliquot showed complete disappearance of 6-chloro-1,4-naphthoquinone. The resulting precipitate was collected by filtration, and washed with acetic acid (200 mL) and hexane (2×300 mL) and air dried to yield the 2,3,6-trichloro-2,3-dihydro-1,4-naphthoquinone (157 g). The solid was transferred into a flask equipped with a mechanical stirrer and reflux condenser. Sodium acetate (98.4 g) and acetic acid (1.5 L) were added, and into the suspension was bubbled chlorine gas. The mixture was brought to reflux and maintained there for 2 hours. The cooled mixture was poured over water (3.5 L), and the resulting precipitate was collected by filtration, and was washed with water (2×500 mL), air dried and then vacuum dried over phosphorus pentoxide, to yield 2,3,6-trichloro-1,4-naphthoquinone (139 g), mp 147.5°–148.5° C.

Similarly, using the above procedure are prepared:
6-bromo-2,3-dichloro-1,4-naphthoquinone;
6-fluoro-2,3-dichloro-1,4-naphthoquinone;
6-methyl-2,3-dichloro-1,4-naphthoquinone;
6-i-propyl-2,3-dichloro-1,4-naphthoquinone;
6-phenyl-2,3-dichloro-1,4-naphthoquinone; and
6-benzyl-2,3-dichloro-1,4-naphthoquinone.

Preparation 11

(Preparation of compounds of formula (VI) wherein $R^3$ is 6-chloro)

To a mechanically stirred solution of sodium methoxide (55.5 g) in anhydrous methanol (1.5 L) under a blanket of nitrogen was added 2,3,6-trichloro-1,4-naphthoquinone from Preparation 10 (130 g) as rapidly as possible. The temperature rose to 50° C. during the addition, and the reaction was then heated to reflux for 1 hour. The mixture was cooled and acidified with 6M hydrochloric acid to give a brilliant yellow color. After the addition of water (300 mL), the reaction mixture was filtered, and the precipitate was washed with aqueous methanol (4:1 water-methanol) until the filtrate was yellow-orange. The precipitate was air dried to yield 6-chloro-2,3-dimethoxy-1,4-naphthoquinone (102 g), mp 125°–126° C.

Similarly, using the above procedure, the following compounds are prepared:
6-bromo-2,3-dimethoxy-1,4-naphthoquinone;
6-fluoro-2,3-dimethoxy-1,4-naphthoquinone;
6-chloro-2,3-diethoxy-1,4-naphthoquinone;
6-methyl-2,3-dimethoxy-1,4-naphthoquinone;
6-i-propyl-2,3-dimethoxy-1,4-naphthoquinone;
6-phenyl-2,3-dimethoxy-1,4-naphthoquinone; and
6-benzyl-2,3-dimethoxy-1,4-naphthoquinone.

Preparation 12

A. To a solution of sodium-n-butoxide (25.8 g) in dry dimethylformamide (125 ml) was added 2,3,6-trichloro-1,4-naphthoquinone (28 g) in one amount. The mixture was refluxed for 2 hours, then cooled, acidified with 6M hydrochloric acid and evaporated. The residue was chromatographed over silica gel using dichloromethane as eluant to yield 2,3-di-n-butyloxy-6-chloro-1,4-naphthoquinone (12.3 g) as a red oily solid.

B. Simlarly, proceeding as above in Part A, substituting the appropriate compound for 2,3,6-trichloro-1,4-naphthoquinone and the appropriate sodium alkoxide for sodium-n-butoxide, the following compounds are prepared:
6-chloro-2,3-di-i-butoxy-1,4-naphthoquinone;
6-chloro-2,3-(2,2-dimethylpropoxy)-1,4-naphthoquinone;
2,3-di-s-butoxy-1,4-naphthoquinone;
2,3-di(2,2-dimethylpropoxy)-1,4-naphthoquinone; and
2,3-di-n-hexyloxy-1,4-naphthoquinone.

C. Similarly, proceeding as above in Part A, substituting the appropriate sodium salt of alkyl mercaptan for sodium-n-butoxide, the following compounds, for example, are prepared:
6-chloro-2,3-dimethylthio-1,4-naphthoquinone;
6-chloro-2,3-di-i-propylthio-1,4-naphthoquinone;
6-chloro-2,3-di-n-hexylthio-1,4-naphthoquinone; and
2,3-dimethylthio-1,4-naphthoquione.

Preparation 13

(Compound of formula (VI) wherein $R^3$ is hydrogen)

To a mechanically stirred solution of sodium methoxide (11.1 g) in anhydrous methanol (200 mL) under a blanket of nitrogen was added 2,3-dichloro-1,4-naphthoquinone (22.7 g) as rapidly as possible. The temperature rose to 50° C. during the addition, and the reaction was then heated to reflux for 1 hour. The mixture was cooled and acidified with 6M hydrochloric acid to give a brilliant yellow color. After the addition of water (800 mL), the reaction mixture was filtered, and the precipitate was washed with aqueous methanol (4:1 water-methanol) until the filtrate was yellow-orange. The precipitate was air dried to yield 21.2 g of 2,3-dimethoxy-1,4-naphthoquinone, m.p. 116°–117° C.

Similarly, substituting the appropriate sodium alkoxide for sodium methoxide the following compounds are prepared.
2,3-diethoxy-1,4-naphthoquinone;
2,3-di-n-propoxy-1,4-naphthoquinone;

EXAMPLE 1

A. A solution of 6-chloro-2,3-dimethoxy-1,4-naphthoquinone (50.5 g, 200 mmol) in tetrahydrofuran (500 mL) was hydrogenated at atmospheric pressure over palladium-on-charcoal (10%, 5.0 g) until the solution was colorless, approximately 4 hours.

B. While still under a blanket of hydrogen, a solution of acetic anhydride (47 mL) pyridine (40 mL) and DMAP (1.22 g) in tetrahydrofuran (50 mL) was added to the mixture. After stirring for 1 hour, the mixture was evaporated. The residue was dissolved in ether (500 mL) and was washed with 1M HCl (3×250 mL) and with brine (2×250 mL). The organic layer was dried over sodium sulfate, filtered, and evaporated to give an oil which crystallized at high vacuum. Recrystallization from ether-petroleum ether afforded 6-chloro-1,4-diacetyloxy-2,3-dimethoxynaphthalene, m.p. 93°–94° C.

Similarly, using the above procedure substituting the appropriate compound of formula (VI) for 6-chloro-2,3-dimethoxy-1,4-naphthoquinone, where appropriate, and the appropriate acid anhydride for acetic anhydride, where appropriate, the following compounds are prepared:
6-chloro-2,3-dimethoxy-1,4-di-n-propanoyloxynaphthalene;
6-chloro-2,3-dimethoxy-1,4-di-i-butanoyloxynaphthalene;
6-chloro-2,3-dimethoxy-1,4-di(2,2-dimethylpropanoyloxy)naphthalene;
6-chloro-2,3-dimethoxy-1,4-di-n-octanoyloxynaphthalene;
6-chloro-2,3-di-n-butoxy-1,4-diacetyloxynaphthalene;
6-chloro-2,3-di-s-butoxy-1,4-diacetyloxynaphthalene;
6-chloro-1,3-di(2,2-dimethylpropoxy)-1,4-diacetyloxynaphthalene;
2,3-di-n-butoxy-1,4-di-n-pentoyloxynaphthalene;
6-chloro-2,3-di-n-propoxy-1,4-dipropanoyloxynaphthalene;

6-chloro-2,3-di-i-propoxy-1,4-dioctanoyloxynaphthalene;
6-bromo-2,3-dimethoxy-1,4-diacetyloxynaphthalene;
6-fluoro-2,3-dimethoxy-1,4-diacetyloxynaphthalene;
5-chloro-2,3-dimethoxy-1,4-diacetyloxynaphthalene;
5-cyano-2,3-dimethoxy-1,4-diacetyloxynaphthalene;
6-cyano-2,3-dimethoxy-1,4-diacetyloxynaphthalene;
6-methylamino-2,3-dimethoxy-1,4-diacetyloxynaphthalene;
6-diethylamino-2,3-dimethoxy-1,4-dipropanoyloxynaphthalene;
6-ethylmethylamino-2,3-dimethoxy-1,4-di-n-butanoyloxynaphthalene;
6-methoxy-2,3-dimethoxy-1,4-di-n-pentanoyloxynaphthalene;
6-ethoxy-2,3-diethoxy-1,4-di-n-hexanoyloxynaphthalene;
6-i-butoxy-2,3-dimethoxy-1,4-di(2,2-dimethylpropanoyloxy)naphthalene;
6-phenylethoxy-2,3-dimethoxy-1,4-diacetyloxynaphthalene;
6-methyl-2,3-dimethoxy-1,4-diacetyloxynaphthalene;
6-i-propyl-2,3-dimethoxy-1,4-di-n-octanoyloxynaphthalene;
6-phenyl-2,3-dimethoxy-1,4-diacetyloxynaphthalene;
6-benzyl-2,3-dimethoxy-1,4-dipropanoyloxynaphthalene;
5-chloro-2,3-di-n-pentyloxy-1,4-di-n-butanoyloxynaphthalene;
5-chloro-2,3-di-s-pentyloxy-1,4-diacetyloxynaphthalene;
5-chloro-2,3-di-n-hexyloxy-1,4-di-n-octanoyloxynaphthalene;
5-chloro-2,3-di-i-hexyloxy-1,4-diacetyloxynaphthalene;
6-chloro-2,3-dimethylthio-1,4-diacetyloxynaphthalene;
6-chloro-2,3-di-i-propylthio-1,4-diacetyloxynaphthalene;
6-chloro-2,3-di-n-hexylthio-1,4-diacetyloxynaphthalene;
2,3-dimethoxy-6-(2-chlorophenylthio)-1,4-diacetyloxynaphthalene;
2,3-dimethoxy-5-(3-chlorophenylthio)-1,4-diacetyloxynaphthalene;
2,3-dimethoxy-6-(4-chlorophenylthio)-1,4-diacetyloxynaphthalene;
2,3-dimethoxy-5-(2,6-dichlorophenylthio)-1,4-diacetyloxynaphthalene;
2,3-dimethoxy-5-(4-fluorophenylthio)-1,4-diacetyloxynaphthalene;
2,3-dimethoxy-5-(2-bromophenylthio)-1,4-diacetyloxynaphthalene;
2,3-dimethoxy-6-(4-bromophenylthio)-1,4-diacetyloxynaphthalene;
2,3-diethoxy-6-(4-methoxyphenylthio)-1,4-diacetyloxynaphthalene;
2,3-dipropoxy-6-(4-nitrophenylthio)-1,4-diacetyloxynaphthalene;
2,3-di-n-butoxy-6-(2-ethylphenylthio)-1,4-diacetyloxynaphthalene;
2,3-di-n-pentyloxy-6-pyridin-2-ylthio-1,4-diacetyloxynaphthalene;
2,3-di-n-hexyloxy-6-pyridin-4-ylthio-1,4-diacetyloxynaphthalene; and
2,3-dimethoxy-5-(4-acetylaminophenylthio)-1,4-diacetyloxynaphthalene.

EXAMPLE 2

A solution of 2,3-dimethoxy-1,4-naphthoquinone (20.0 g) in tetrahydrofuran (150 mL) was hydrogenated at atmospheric pressure over Pd-C (10%, 0.5 g) until the solution was colorless, approximately 4 hours. While still under a blanket of hydrogen, a solution of acetic anhydride (20 mL) and pyridine (18 mL) in tetrahydrofuran (50 mL) was added to the mixture. After stirring for 1 hour, the mixture was evaporated. The residue was dissolved in ether (100 mL) and was washed with 1M hydrochloric acid (3×50 mL) and with brine (2×50 mL). The organic layer was dried over sodium sulfate, filtered, and evaporated. Recrystallization from ether afforded 2,3-dimethoxy-1,4-diacetyloxynaphthalene (22.5 g), m.p. 138°–139° C.

Similarly proceeding as above, substituting the appropriate compound for 2,3-dimethoxy-1,4-naphthoquinone and the appropriate acid anhydride, where appropriate, for acetic anhydride, the following compounds, for example, are prepared:
2,3-di-n-propoxy-1,4-di-n-propanoyloxynaphthalene;
2,3-di-s-butoxy-1,4-di-i-butanoyloxynaphthalene;
2,3-di(2,2-dimethylpropoxy)-1,4-di-n-pentanoyloxynaphthalene;
2,3-di-n-hexyloxy-1,4-di(2,2-dimethylpropanoyloxy)-naphthalene;
2,3-dimethoxy-1,4-di-n-propanoyloxynaphthalene;
2,3-diethoxy-1,4-diacetyloxynaphthalene; and
2,3-dimethylthio-1,4-diacetyloxynaphthalene.

EXAMPLE 3

(Preparation of Compounds of Formula (I) where $R^3$ is phenylsulfinyl)

Forty percent (w/v) peracetic acid in acetic acid (1 ml) is added over 30 minutes to a solution of 2,3-dimethoxy-5-phenylthio-1,4-diacetyloxynaphthalene (0.98 g, 3 mmol) in methylene chloride (15 ml). Excess peracetic acid is destroyed by the addition of a few milligrams of 5% palladium on carbon and the mixture filtered through a celite bed. The filtrate is concentrated in vacuo and the residue recrystallized from methanol giving 0.59 g of 2,3-dimethoxy-5-phenylsulfinyl-1,4-diacetyloxynaphthalene.

Similarly, using either peracetic acid or m-chloroperbenzoic acid, the following compounds are prepared from the respective thio compounds:
2,3-dimethoxy-5-(imidazol-2-ylsulfinyl)-1,4-diacetyloxynaphthalene;
2,3-dimethoxy-6-(2-chlorophenylsulfinyl)-1,4-diacetyloxynaphthalene;
2,3-dimethoxy-5-(3-chlorophenylsulfinyl)-1,4-diacetyloxynaphthalene;
2,3-dimethoxy-6-(4-chlorophenylsulfinyl)-1,4-diacetyloxynaphthalene;
2,3-dimethoxy-5-(2,6-dichlorophenylsulfinyl)-1,4-diacetyloxynaphthalene;
2,3-dimethoxy-5-(4-fluorophenylsulfinyl)-1,4-diacetyloxynaphthalene;
2,3-dimethoxy-5-(2-bromophenylsulfinyl)-1,4-diacetyloxynaphthalene;
2,3-dimethoxy-5-(4-bromophenylsulfinyl)-1,4-diacetyloxynaphthalene;
2,3-diethoxy-6-(4-methoxyphenylsulfinyl)-1,4-diacetyloxynaphthalene;
2,3-dipropoxy-6-(4-nitrophenylsulfinyl)-1,4-diacetyloxynaphthalene;

2,3-di-n-butoxy-6-(2-ethylphenylsulfinyl)-1,4-diacetyloxynaphthalene;
2,3-dimethoxy-6-(pyrimidin-2-ylsulfinyl)-1,4-diacetyloxynaphthalene;
2,3-dimethoxy-5-(pyrimidin-4-ylsulfinyl)-1,4-diacetyloxynaphthalene;
2,3-dimethoxy-6-methylsulfinyl-1,4-diacetyloxynaphthalene;
2,3-dimethoxy-5-benzylsulfinyl-1,4-diacetyloxynaphthalene; and
2,3-dimethoxy-5-methoxycarbonylmethylsulfinyl-1,4-diacetyloxynaphthalene.

EXAMPLE 4

2,3-Dimethoxy-5-phenylsulfonyl-1,4-diacetyloxynaphthalene (Preparation of Compound of Formula (I) where $R^3$ is phenylsulfonyl)

A mixture of m-chloroperbenzoic acid (300 mg) and 2,3-dimethoxy-5-phenylthio-1,4-naphthoquinone (200 mg, 0.61 mmol) in methylene chloride (5 ml) is stirred at 22° C. for 16 hours and the resulting solution then passed through an alumina column (10 g of Activity 1) eluting with chloroform. The eluates are concentrated to dryness and the residue is crystallized from isopropanol giving 95 mg of 2,3-dimethoxy-5-phenylsulfonyl-1,4-diacetyloxynaphthalene.

What is claimed is:

1. A composition in a form suitable for topical administration for relieving the condition of psoriasis which comprises a pharmaceutically acceptable, non-toxic carrier and a psoriasis relieving amount of a compound of the formula

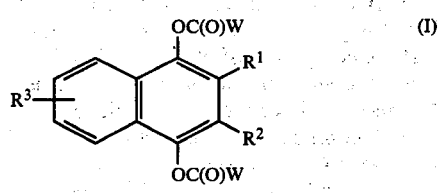

wherein:
$R^1$ and $R^2$ are lower alkoxy of one to six carbon atoms or lower alkylthio of one to six carbon atoms;
$R^3$ is hydrogen, lower alkyl of one to six carbon atoms, lower alkoxy of one to six carbon atoms, phenyl optionally substituted by one or more lower alkyl, lower alkoxy, halo, lower acyl, lower acyloxy, cyano, nitro or lower acylamino, phenyl lower alkyl optionally substituted by one or more lower alkyl, lower alkoxy, halo, lower acyl, lower acyloxy, cyano, nitro or lower acylamino, phenyl lower alkoxy optionally substituted by one or more lower alkyl, lower alkoxy, halo, lower acyl, lower acyloxy, cyano, nitro or lower acylamino, amino, lower alkylamino, lower dialkylamino, halo, cyano, or $S(O)_nR$ wherein R is lower alkyl of one to six carbon atoms; phenyl optionally substituted by one or more lower alkyl, lower alkoxy, halo, lower acyl, lower acyloxy, cyano, nitro or lower acylamino; phenyl lower alkyl optionally substituted by one or more lower alkyl, lower alkoxy, halo, lower acyl, lower acyloxy, cyano, nitro or lower acylamino; or heterocyclic aryl selected from the group consisting of thiapyranyl, benzothiapyranyl, furyl, pyrrolyl, imidazolyl, pyrazolyl, pyridinyl, pyrimidinyl, indolyl, quinolinyl and indazolyl wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and
W is alkyl of one to seven carbon atoms.

2. The composition according to claim 1 wherein the compound is

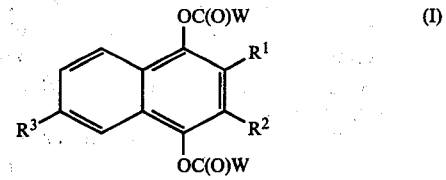

wherein $R^1$, $R^2$, $R^3$, and W are as defined in claim 1.

3. The composition according to claim 2 wherein $R^1$ and $R^2$ are lower alkoxy of one to six carbon atoms.

4. The composition according to claim 3 wherein $R^3$ is selected from the group consisting of hydrogen, halo, cyano, and alkoxy of one to four carbon atoms.

5. The composition according to claim 4 wherein $R^3$ is selected from the group consisting of hydrogen, fluoro, chloro and bromo.

6. The composition according to claim 4 wherein $R^3$ is cyano.

7. The composition according to claim 5 wherein the compound is 2,3-dimethoxy-1,4-acetyloxynaphthalene.

8. The composition according to claim 5 wherein the compound is 6-bromo-2,3-dimethoxy-1,4-acetyloxynaphthalene.

9. The composition of claim 5 wherein the compound is 6-chloro-2,3-dimethoxy-1,4-acetyloxynaphthalene.

10. A composition of claim 5 wherein the compound is 6-chloro-2,3-di-n-butoxy-1,4-acetyloxynaphthalene.

11. The composition according to claim 2 wherein $R^1$ and $R^2$ are lower alkylthio of one to six carbon atoms.

12. A method of treating psoriasis in mammals which comprises applying an effective amount of a compound of the formula

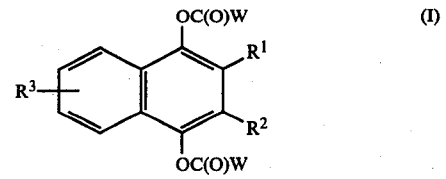

wherein:
$R^1$ and $R^2$ are lower alkoxy of one to six carbon atoms or lower alkylthio of one to six carbon atoms;
$R^3$ is hydrogen, lower alkyl of one to six carbon atoms, lower alkoxy of one to six carbon atoms, phenyl optionally substituted by one or more lower alkyl, lower alkoxy, halo, lower acyl, lower acyloxy, cyano, nitro or lower acylamino, phenyl lower alkyl optionally substituted by one or more lower alkyl, lower alkoxy, halo, lower acyl, lower acyloxy, cyano, nitro or lower acylamino, phenyl lower alkoxy optionally substituted by one or more lower alkyl, lower alkoxy, halo, lower acyl, lower acyloxy, cyano, nitro or lower acylamino, amino, lower alkylamino, lower dialkylamino, halo, cyano, or $S(O)_nR$ wherein R is lower alkyl of one to six carbon atoms; phenyl optionally substituted by one or more lower alkyl, lower alkoxy, halo, lower acyl, lower acyloxy, cyano, nitro or lower acylamino; phenyl lower alkyl optionally substituted by one or more lower alkyl, lower alkoxy, halo, lower acyl, lower acyloxy, cyano, nitro or lower acylamino; or heterocyclic aryl selected from the group consisting of thiapyranyl, benzothiapyranyl, furyl, pyrrolyl, imidazolyl, pyrazolyl, pyridinyl, pyrimidinyl, indolyl, quinolinyl and indazolyl wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and W is alkyl of one to seven carbon atoms.

13. A method according to claim 12 wherein $R^1$ and $R^2$ are lower alkoxy of one to six carbon atoms.

14. A method according to claim 12 wherein $R^1$ and $R^2$ are lower alkylthio of one to six carbon atoms.

15. A compound of the formula

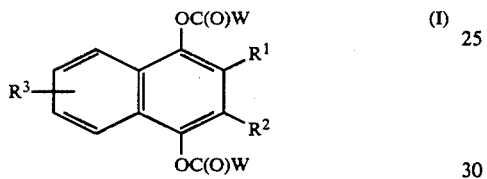

wherein:
$R^1$ and $R^2$ are lower alkoxy of one to six carbon atoms or lower alkylthio of one to six carbon atoms;

$R^3$ is hydrogen, lower alkyl of one to six carbon atoms, lower alkoxy of one to six carbon atoms, phenyl optionally substituted by one or more lower alkyl, lower alkoxy, halo, lower acyl, lower acyloxy, cyano, nitro or lower acylamino, phenyl lower alkyl optionally substituted by one or more lower alkyl, lower alkoxy, halo, lower acyl, lower acyloxy, cyano, nitro or lower acylamino, phenyl lower alkoxy optionally substituted by one or more lower alkyl, lower alkoxy, halo, lower acyl, lower acyloxy, cyano, nitro or lower acylamino, amino, lower alkylamino, lower dialkylamino, halo, cyano, or $S(O)_nR$ wherein R is lower alkyl of one to six carbon atoms; phenyl optionally substituted by one or more lower alkyl, lower alkoxy, halo, lower acyl, lower acyloxy, cyano, nitro or lower acylamino; phenyl lower alkyl optionally substituted by one or more lower alkyl, lower alkoxy, halo, lower acyl, lower acyloxy, cyano, nitro or lower acylamino; or heterocyclic aryl selected from the group consisting of thiapyranyl, benzothiapyranyl, furyl, pyrrolyl, imidazolyl, pyrazolyl, pyridinyl, pyrimidinyl, indolyl, quinolinyl and indazolyl wherein the heterocyclic aryl is optionally substituted by one or more substituents selected from the group consisting of lower alkyl, lower alkoxy, halo and cyano and the pharmaceutically acceptable acid addition salts thereof; and n is 0, 1 or 2; and W is alkyl of one to seven carbon atoms; with the proviso that $R^3$ is not hydrogen when $R^1$ and $R^2$ are methoxy and W is methyl.

16. A compound of claim 15 of the formula

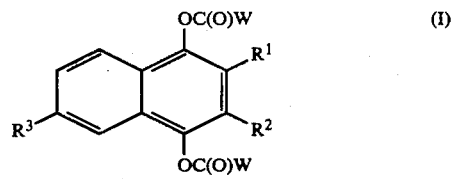

wherein $R^1$, $R^2$, $R^3$ and W are as defined in claim 15.

17. A compound of claim 16 wherein $R^1$ and $R^2$ are lower alkoxy of one to six carbon atoms.

18. A compound of claim 17 wherein $R^3$ is selected from the group consisting of fluoro, chloro and bromo.

19. A compound of claim 17 wherein $R^3$ is cyano.

20. A compound of claim 18 which is 6-chloro-2,3-dimethoxy-1,4-acetyloxynaphthalene.

21. A compound of claim 18 which is 6-chloro-2,3-di-n-butoxy-1,4-acetyloxynaphthalene.

22. A compound of claim 16 wherein $R^1$ and $R^2$ are lower alkylthio of one to six carbon atoms.

* * * * *

UNITED STATES PATENT AND TRADEMARK OFFICE
CERTIFICATE OF CORRECTION

PATENT NO. : 4,466,981
DATED : August 21, 1984
INVENTOR(S) : Gordon H. Jones et al.

It is certified that error appears in the above-identified patent and that said Letters Patent are hereby corrected as shown below:

In Claim 7, line 2, "-1,4-acetyloxynaphthalene" should read ---1,4-diacetyloxynaphthalene--.

In Claim 8, line 2, "-1,4-acetyloxynaphthalene" should read ---1,4-diacetyloxynaphthalene--.

In Claim 9, line 2, "-1,4-acetyloxynaphthalene" should read ---1,4-diacetyloxynaphthalene--.

In Claim 10, line 2, "-1,4-acetyloxynaphthalene" should read ---1,4-diacetyloxynaphthalene--.

In Claim 20, line 2, "-1,4-acetyloxynaphthalene" should read ---1,4-diacetyloxynaphthalene--.

In Claim 21, line 2, "-1,4-acetyloxynaphthalene" should read ---1,4-diacetyloxynaphthalene--.

Signed and Sealed this
Twenty-third Day of December, 1986

*Attest:*

DONALD J. QUIGG

*Attesting Officer*   *Commissioner of Patents and Trademarks*